(12) United States Patent
Braillard et al.

(10) Patent No.: US 10,326,152 B2
(45) Date of Patent: Jun. 18, 2019

(54) SYSTEM FOR MEASURING THE HYGROMETRY OF AN ION EXCHANGE MEMBRANE IN A FUEL CELL

(71) Applicants: COMPAGNIE GENERALE DES ETABLISSEMENTS MICHELIN, Clermont-Ferrand (FR); MICHELIN RECHERCHE ET TECHNIQUE S.A., Granges-Paccot (CH)

(72) Inventors: Vincent Braillard, Clermont-Ferrand (FR); Gino Paganelli, Clermont-Ferrand (FR)

(73) Assignee: Compagnie Generale des Etablissements Michelin, Clermont-Ferrand (FR)

(*) Notice: Subject to any disclaimer, the term of this patent is extended or adjusted under 35 U.S.C. 154(b) by 4 days.

(21) Appl. No.: 15/537,474

(22) PCT Filed: Dec. 17, 2015

(86) PCT No.: PCT/EP2015/080172
§ 371 (c)(1),
(2) Date: Jun. 19, 2017

(87) PCT Pub. No.: WO2016/097114
PCT Pub. Date: Jun. 23, 2016

(65) Prior Publication Data
US 2017/0352895 A1 Dec. 7, 2017

(30) Foreign Application Priority Data
Dec. 19, 2014 (FR) .................................... 14 62904

(51) Int. Cl.
*G01R 27/08* (2006.01)
*H01M 8/04* (2016.01)
(Continued)

(52) U.S. Cl.
CPC ............ *H01M 8/04* (2013.01); *G01N 27/048* (2013.01); *H01M 8/04529* (2013.01);
(Continued)

(58) Field of Classification Search
CPC .... G01N 27/048; G01N 17/00; G01N 17/006; G01N 17/02; G01N 27/02; G01N 27/04;
(Continued)

(56) References Cited

U.S. PATENT DOCUMENTS

2002/0196025 A1 12/2002 Freeman et al. ............... 324/426
2005/0287402 A1* 12/2005 Maly ................. H01M 8/04291
702/65
(Continued)

FOREIGN PATENT DOCUMENTS

FR         2 982 374 A1    5/2013
WO       WO 02/35677 A1   5/2002
WO     WO 2014/046028 A1  3/2014

OTHER PUBLICATIONS

Mar. 7, 2016 International Search Report and Written Opinion in International Patent Appln. No. PCT/EP2015/080172.

*Primary Examiner* — Huy Q Phan
*Assistant Examiner* — Raul J Rios Russo
(74) *Attorney, Agent, or Firm* — Venable LLP

(57) ABSTRACT

A system for measuring a moisture content of an ion-exchange membrane in a fuel-cell stack is provided. The fuel-cell stack includes N electrochemical cells separated by bipolar plates, with N being a natural integer. The system includes a current generator, a voltage measurement device, and an impedance measurement device. The current generator enables a current to be applied to the fuel-cell stack. The voltage measurement device measures voltages of the cells of the fuel-cell stack. The impedance measurement device determines an impedance of an ion-exchange membrane (Continued)

according to a voltage ripple measured by the voltage measurement device across terminals of a corresponding one of the cells of the fuel-cell stack when the current is applied by the current generator. The impedance measurement device is installed in the voltage measurement device.

10 Claims, 2 Drawing Sheets

(51) Int. Cl.
*H01M 8/04492* (2016.01)
*H01M 8/04537* (2016.01)
*G01N 27/04* (2006.01)
*G01R 31/389* (2019.01)

(52) U.S. Cl.
CPC ... *H01M 8/04552* (2013.01); *H01M 8/04641* (2013.01); *G01R 31/389* (2019.01)

(58) Field of Classification Search
CPC .... G01L 1/10; G01L 1/20; G01L 1/22; G01R 27/00
USPC ... 324/600, 76.11–76.83, 649, 691, 693, 694
See application file for complete search history.

(56) References Cited

U.S. PATENT DOCUMENTS

| | | | |
|---|---|---|---|
| 2006/0074574 A1* | 4/2006 | Gasda | H01M 8/04559 702/63 |
| 2009/0286109 A1* | 11/2009 | Araki | H01M 8/04126 429/483 |
| 2011/0027679 A1 | 2/2011 | Nonobe | 429/432 |
| 2014/0188414 A1* | 7/2014 | Jeong | H01M 8/04649 702/63 |
| 2014/0227571 A1 | 8/2014 | Paganelli et al. | 429/90 |
| 2014/0300367 A1 | 10/2014 | Paganelli et al. | 324/434 |
| 2015/0024295 A1* | 1/2015 | Hibino | H01M 8/04835 429/413 |
| 2015/0136352 A1 | 5/2015 | Paganelli et al. | H01M 8/04074 |
| 2015/0325871 A1 | 11/2015 | Paganelli et al. | H01M 8/04671 |
| 2017/0324105 A1 | 11/2017 | Braillard et al. | |
| 2017/0338501 A1 | 11/2017 | Paganelli et al. | |
| 2017/0352896 A1 | 12/2017 | Braillard et al. | |

* cited by examiner

SYSTEM FOR MEASURING THE HYGROMETRY OF AN ION EXCHANGE MEMBRANE IN A FUEL CELL

TECHNICAL FIELD

The present invention relates to the field of fuel cell stacks and, in particular, to systems for monitoring such stacks. More particularly, it pertains to devices for measuring voltages in fuel cell stacks.

RELATED ART

Fuel cell stacks are becoming increasingly successful in numerous applications. They are of particular interest to the automotive industry in the context of electric vehicle development, since they constitute clean electricity generators of lower weight than battery-type electrochemical accumulators, and exhibit a high level of efficiency.

In a fuel cell stack, electricity is produced by way of a dual chemical reaction: the oxidation of a fuel, for example hydrogen, on one electrode, coupled with the reduction of an oxidant, for example oxygen, on another electrode. Thus, a fuel cell stack generally includes an anode and a cathode between which a membrane is positioned, forming a membrane electrode assembly (MEA). Various types of membranes may be used, and fluorinated polymer membranes are known, for example.

In order to allow the chemical reaction to take place, it is necessary for the membrane to be a good conductor of protons. Now, this proton conduction improves as the moisture content of the membrane increases. However, it is necessary to ensure that there is not an excess of this water either, since liquid water may obstruct the passage of the gas. It therefore appears to be advantageous, in the light of these aspects, to be able to monitor the moisture content of the membrane during the operation of a fuel cell stack.

Furthermore, when using fuel cell stacks under very low temperature conditions, it has been observed that it is advantageous to dry out the membrane when shutting down the fuel cell stack, so as to facilitate a later cold start. Specifically, the membrane constitutes the sole "refuge" in the stack where water does not freeze when the stack is in a very cold environment. Upon contact with all other components of the stack core, water freezes immediately and forms blockages that hinder the operation of the stack. In order to be able to make use of this accumulator, it is necessary to be able to absorb water (the membrane has a limited capacity to absorb water, referred to as the "water absorption capability [mg/cm$^2$]", hence the requirement to dry out the membrane before a cold start. It is therefore also advantageous to be able to measure the moisture content of the membrane after shutting down the fuel cell stack.

In the prior art, various means for measuring the moisture content of a fuel cell stack are known. However, these known means are generally independent of any other functionality, and hence require additional installation in a fuel cell stack system which already includes a large number of measurement and/or management devices.

The present invention therefore aims to provide a measurement system that allows this drawback to be remedied.

BRIEF DESCRIPTION OF THE INVENTION

The invention thus relates to a system for measuring the moisture content of an ion exchange membrane in a fuel cell stack including N electrochemical cells separated by bipolar plates, where N is a natural integer, the system comprising:
- a current generator allowing a current to be applied to the fuel cell stack;
- a device for measuring voltages of the cells; and
- means for determining the impedance of a membrane according to a voltage ripple measured by the measurement device across the terminals of the corresponding cell when a current is applied by the current generator, these means being installed in the device for measuring voltages of the cells.

The membrane of a fuel cell stack, in particular of PEMFC type, is a solid polymer layer. Now, it is known that the higher the moisture content of a solid, the lower its impedance. Consequently, by passing a current through the membrane and measuring the resulting voltage ripples, it is possible to determine the resistance of the membrane and hence its moisture content.

Furthermore, installing the means for determining the impedance directly inside the device for measuring voltages of the cells makes it possible to simplify the installation, and thus makes it possible to incorporate multiple functions within one and the same system without overcomplexifying the construction of the fuel cell stack system.

In one advantageous embodiment, the current generator applies a current at a frequency of 1000 hertz. In this embodiment, the moisture content of the membrane is sufficiently low if the resistance of the membrane is of the order of 2.5 milliohms per cell with 200 cm$^2$ of active surface area, namely 40 milliohms for a stack of 16 cells.

The invention thus relates to a device for measuring voltages of cells in a fuel cell stack including N electrochemical cells separated by bipolar plates, where N is a natural integer, the system comprising:
- at least two voltage measurement modules, each module being capable of measuring M voltages across a set of contiguous cells of the fuel cell stack, where M is a natural integer smaller than or equal to N/2, the group of cells measured by the first module being adjacent to the group of cells measured by the second module;
- an electronic computer; and
- a wired communication bus connecting the at least two measurement devices in series to the computer, each of the measurement modules comprising:
- mechanical means for fastening the module to the fuel cell stack;
- electronic means for measuring voltage;
- electrical means for connecting the bipolar plates to at least one electronic means for measuring voltage;
- means for connecting the electronic means for measuring voltage to the communication bus.

Additionally, preferably, the mechanical means for fastening the module to the fuel cell stack and the electrical connection means are combined. Thus, in one particular embodiment, these means include terminals, for example Faston®-type female terminals, allowing both a mechanical and an electrical connection to be made. These female terminals include two metal portions that are arranged so as to clasp metal lugs formed on the bipolar plates of the stack, allowing the connection to be made.

In one particular embodiment of the invention, each electronic means for measuring voltage measures the voltages of two adjacent cells. Specifically, given the low thickness of the electrochemical cells of a fuel cell stack, it was found to be ergonomically impractical to install means for measuring the individual voltages of each cell. Furthermore, the measurement means have been shown to be sensitive enough that a measurement taken on two cells allows the state of each of the cells to be monitored. Thus, in one particular embodiment, one module effects eight voltage measurements for a set of 16 cells.

In one particular embodiment of the invention, the wired communication bus is a CAN® (controller area network) serial bus, exhibiting robustness characteristics that are useful in the context of a device such as that of the present invention. In another particular embodiment, an I2C bus is used.

Furthermore, in another particular embodiment of the invention, the measurement device comprises at least one galvanic isolation device between the wired communication bus and the fuel cell stack. Such a device comprises, for example, an optocoupler. Specifically, the fuel cell stack consists of cells connected in series; depending on its position on the fuel cell stack, each measurement module is therefore at a different potential with respect to the negative pole of the fuel cell stack. It is therefore necessary to implement galvanic isolation between the measurement means and the common communication bus.

In another particular embodiment of the invention, each voltage measurement module includes a different address, or coding, from the other modules. Specifically, and as explained below, this allows the electronic computer to address the requests by means of which measurements are solicited to the various modules.

The electronic computer is used to manage the measurements taken by the device. To achieve this, it communicates with the modules via the wired communication bus, and receives the measurement results by the same means. Throughout the rest of the application, this computer will be referred to as the controller, without however restricting the scope of the term to a specific type of component.

BRIEF DESCRIPTION OF THE FIGURES

Other objectives and advantages of the invention will appear clearly in the following description of a preferred, but non-limiting, embodiment, illustrated by the following figures in which.

DESCRIPTION OF THE BEST EMBODIMENT OF THE INVENTION

Figure 1:
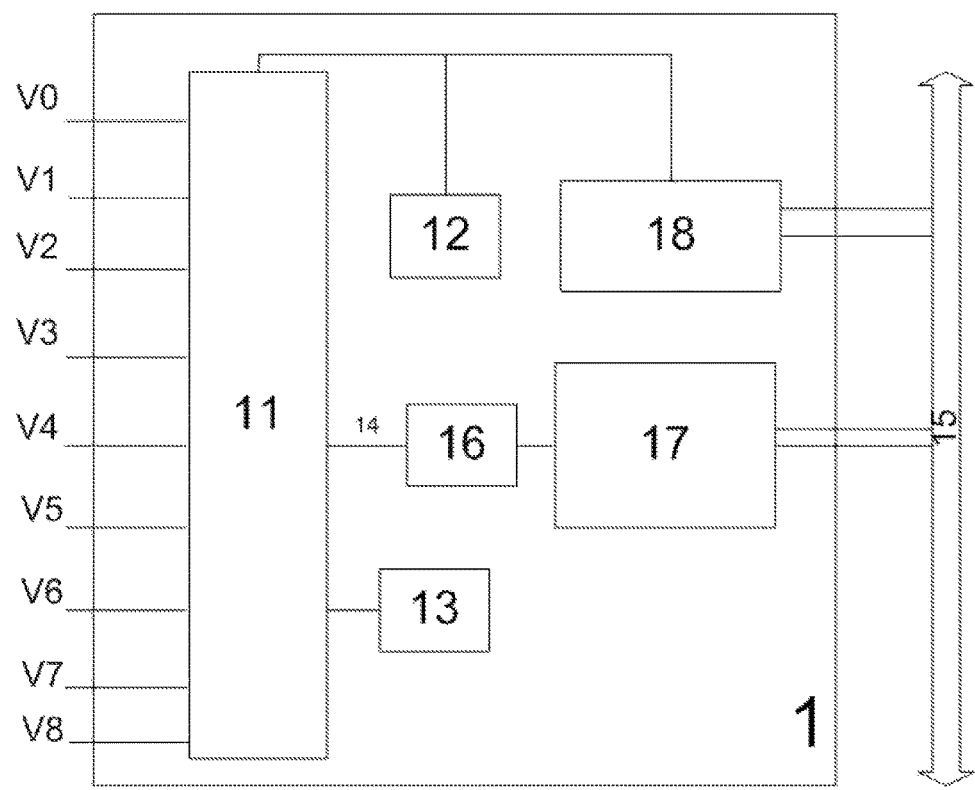
FIG. 1 shows a block diagram of a module used in the context of a device according to the invention.

FIG. 1 shows an example of functional architecture of a voltage measurement device implemented in a system according to the invention.

The module 1 is connected to nine bipolar plates, thereby allowing nine potentials V0 to V8 to be measured. These measurements are taken by analogue-to-digital converters 11. This converter is linked to a reference value 12 that is equal, for example, to 0.5 volts, allowing the measurements transmitted by the assemblies 10 to be compared. The eight voltages present at the terminals of the measured cells are subsequently calculated by the microcontroller 16 by differencing between two successive voltage measurements.

The analogue-to-digital converter 11 is only able to convert positive voltages. However, it is desirable, in one embodiment of the invention, to be able to measure negative voltages as well, thereby making it possible to detect a cell inversion, in particular due to an insufficient supply of hydrogen. In order to overcome this, the converter 11 is also connected to a device 13 allowing an offset voltage to be applied to the measured voltages, before conversion.

Once a measurement has been converted, the result is transmitted to a data bus 14. This bus is, for example, an I2C (inter-integrated circuit) bus or a CAN® bus. This data bus 14 routes the data to a second data bus 15, which subsequently routes the data to a general controller 20 (see FIG. 2). In the event that the buses 14 and 15 are not of the same type, it is advantageous to provide a microcontroller 16 allowing the data to be converted to a format supported by the bus 15. Furthermore, in order to prevent the high voltages present at the fuel cell stack propagating to the bus 15 and damaging certain components, it is advantageous to provide a galvanic isolation device 17, for example an optocoupler.

The overall module 1 is supplied with power by the bus 15. To this end, a voltage-to-voltage converter 18 is installed within the module and connected to the main components. This converter also comprises, in one preferred embodiment, a galvanic isolation device in order to avoid the problem mentioned above.

Figure 2:
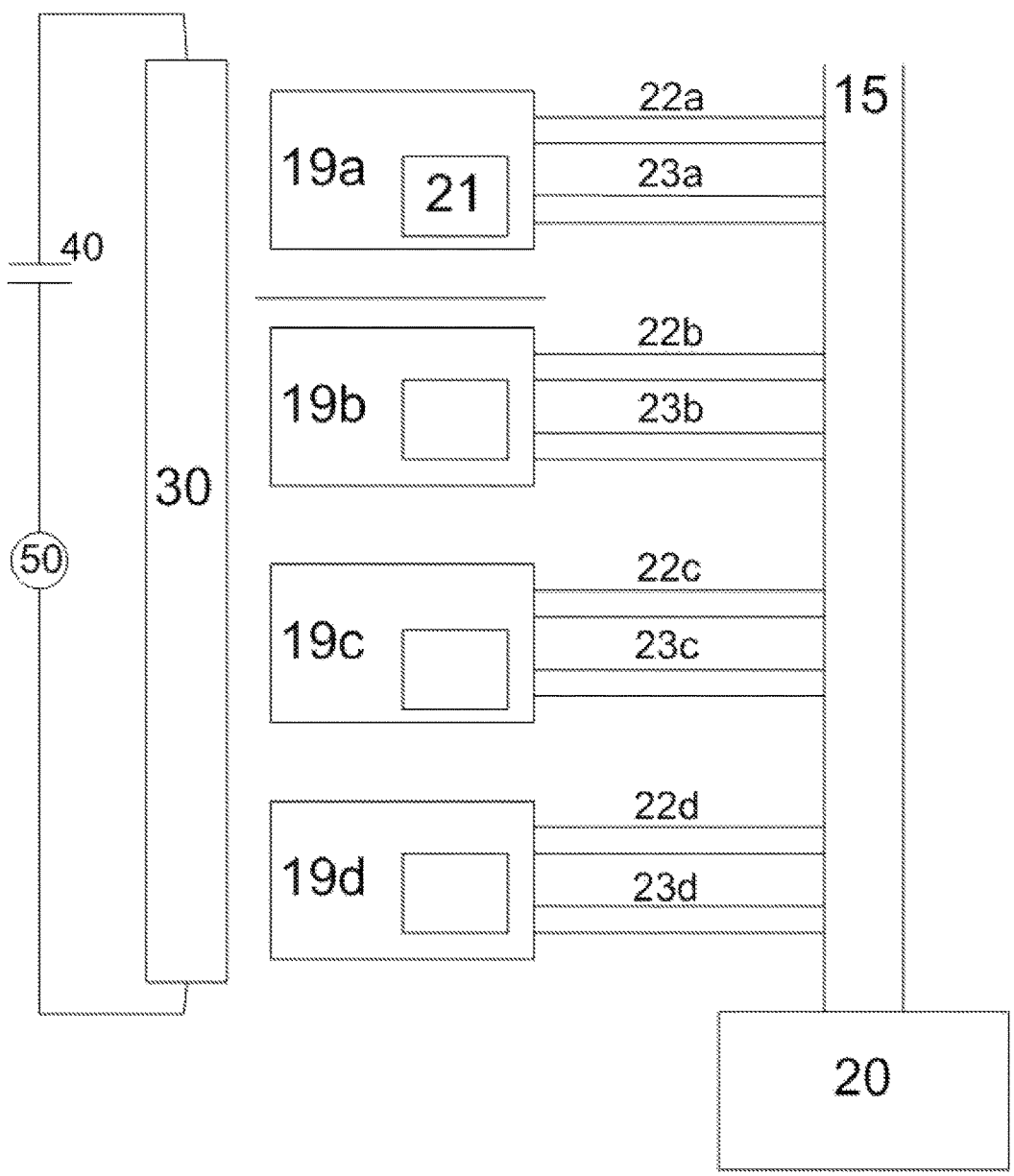
FIG. 2 shows a device according to the invention including four measurement modules.

FIG. 2 shows an exemplary embodiment of a system according to the invention, implementing multiple measurement devices in accordance with that of FIG. 1, these devices being referred to hereinafter as "modules".

This device comprises four modules 19a, 19b, 19c and 19d. Each of the modules is connected to the bus 15 which links them to the controller 20. The number of modules is given here by way of example and is not limiting. Each module is linked to eight cells of the fuel cell stack 30. These links are not shown in the figure for the sake of simplicity. A device with four modules allows, in the event that a converter with eight inputs is used, 32 voltages to be measured. It can therefore be used on a stack of 64 cells in the case that the cell voltages are measured per group of two cells. Each of the modules has an address 21 allowing them to be differentiated. For example, this address is coded on three bits with three states and is physically inscribed on each module through the use of spots of solder allowing electrical connections representing each of the bits to be made.

The controller 20 is the member which manages the operation of the measurement device, and in particular which orders the measurements. Specifically, voltage measurements are not transmitted constantly to the controller, but only upon request.

In the absence of a request, the modules draw from the bus 15, via the corresponding links 22a, 22b, 22c and 22d, only a hold current enabling them to receive the requests and to determine whether they are concerned. However, in the absence of a request, the converter 11 is not activated, therefore no conversion is carried out.

When a measurement is needed, the controller 20 first sends a request over the bus, comprising the address of the module and the position of the cell for which it is desired to receive the voltage. Upon receiving the request, the addressed module leaves its standby state and draws a larger current from the bus 15.

It then proceeds to read the value previously converted and stored at the converter 11, and then triggers a new conversion intended to be used during a later request. The read value is then transferred to the bus 15 via the corresponding link from among the links 23a to 23d, and then communicated to the controller 20.

The controller 20 of the stack is thus capable, according to the measurements received, of determining that the voltages are not locked and that they are not located outside the domain of conventional operation. If a fault is detected, it may be useful to stop the stack in order to prevent any dangerous malfunctioning.

A device according to the invention therefore clearly meets the required demands of simplicity and reliability. Specifically, the bus 15 serves both for communicating data and for supplying power to the modules, thereby allowing measurements to continue to be taken even in the event of malfunctioning of the stack.

The system shown in FIG. 2 comprises a 1 kHz current generator, bearing the reference 50, for measuring impedance. This current is applied to the power poles of the stack 30. It is assumed here that the stack comprises 16 cells. In the case of a larger stack, the current generator is connected to the end poles of the stack, independently of the number of voltage measurement modules. In order to decouple the current generator 50 from the DC voltage that may be present across the terminals of the stack 30, which constitutes a voltage generator, a capacitor 40 is connected in series between the current generator 50 and the poles of the stack 30.

In order to measure the impedance, the 1000 Hz alternating component of the voltage present across the terminals of the cells is used. The voltage measurement device must therefore be fast enough to measure this voltage ripple. In practice, it must be capable of measuring at least at the frequency of 10 kHz. The voltage ripple induced by the 1 kHz current injected at the terminals of the stack increases with impedance. The impedance is determined for each voltage measurement module by dividing the 1 kHz component of the voltage divided by the value of the injected 1 kHz current. The overall impedance for the stack is then calculated by addition of the impedance indicated by each module. The voltage ripple induced by the 1 kHz current is more sensitive and the measurement more accurate when the direct current produced by the stack is low or zero. In general however the stack is dried out when the fuel cell stack is not in operation or operating under low current.

Another advantage linked to the use of the voltage measurement device for determining impedance is that it is possible to determine the moisture content level of each group of two cells, since the voltage measurements are taken at each group of two cells. This may be advantageous for determining the uniformity of the moisture content within the stack, whereas an overall measurement of the impedance at the poles of the stack, as is generally done, gives no indication of the uniformity of the moisture content. This is particularly advantageous for stacks of several tens of cells for which a lack of uniformity in terms of moisture content is liable to occur due to head losses in the manifolds when drying out. It may also be advantageous to set an impedance criterion for the group of two cells with the highest moisture content rather than for the overall stack. Specifically, during a cold start, if the moisture content of the membranes is not uniform within the stack, the membranes with the highest moisture content risk becoming the factor limiting the success of the cold start.

For cost reasons, it is possible for the voltage measurement devices not to be mounted throughout the entire stack but solely on the most sensitive areas that require monitoring, in general the ends. In this configuration, the impedance measurement will be taken only on those cells provided with the voltage measurement device. It will then be sufficient to adapt the target impedance criterion to the number of monitored cells when drying out in preparation for a cold start. For simplicity, the 1 kHz current may, for its part, be injected at the terminals of the stack and will therefore pass through all of the cells, even those which are not monitored, but this causes no particular problems.

The invention claimed is:

1. A moisture measurement system for measuring a moisture content of an ion-exchange membrane in a fuel cell stack that includes N electrochemical cells separated by bipolar plates, where N is a natural integer, the moisture measurement system comprising:
a current generator, connected in series with a capacitor to the fuel cell stack, that enables a current to be applied to the fuel cell stack;
a voltage measurement system for measuring voltages of the cells; and
an impedance measurement device for determining an impedance of a membrane according to a voltage ripple measured by the voltage measurement system across terminals of a corresponding one of the cells when the current is applied by the current generator, the impedance measurement device being installed in the voltage measurement system.

2. The moisture measurement system according to claim 1, wherein the current generator applies the current at a frequency of 1000 hertz.

3. The moisture measurement system according to claim 1, wherein the voltage measurement system includes: (a) at least two voltage measurement modules, each of the modules being arranged to measure M voltages across a set of contiguous cells of the fuel cell stack, where M is a natural integer smaller than or equal to N/2, wherein a group of cells measured by a first one of the modules is adjacent to a group of cells measured by a second one of the modules, (b) an electronic computer, and (c) a wired communication bus connecting the at least two voltage measurement modules in series to the computer, and
wherein each of the voltage measurement modules includes: (a) a fastener that mechanically fastens the module to the fuel cell stack, (b) an electronic voltage device for measuring voltage; (c) an electrical connector that electrically connects the bipolar plates to at least one of the electronic voltage devices for measuring voltage, and (d) a bus connector that connects the electronic voltage device for measuring voltage to the wired communication bus.

4. The moisture measurement system according to claim 3, wherein each of the electronic voltage devices for measuring voltage measures voltages of two adjacent cells.

5. The moisture measurement system according to claim 3, wherein the electrical connector includes terminals that are useable as mechanical fasteners.

6. The moisture measurement system according to claim 5, wherein the electrical connector is structured to interact with metal lugs positioned on the bipolar plates.

7. The moisture measurement system according claim 3, further comprising at least one galvanic isolation device positioned between the wired communication bus and the fuel cell stack.

8. The moisture measurement system according to claim 7, wherein each of the at least one galvanic isolation device includes an optocoupler.

9. The moisture measurement system according to claim 3, wherein each of the voltage measurement modules includes an address that is different from addresses of others of the voltage measurement modules.

10. The moisture measurement system according to claim 3, where M is equal to 8.

* * * * *